US008435756B2

(12) United States Patent  (10) Patent No.: US 8,435,756 B2
Powell et al.  (45) Date of Patent: May 7, 2013

(54) ANIONIC ACID-LABILE SURFACTANTS AND METHODS OF USE

(75) Inventors: Matthew Jacob Powell, Westover, WV (US); Trust Tariro Razunguzwa, Morgantown, WV (US); George Augustine O'Doherty, Morgantown, WV (US); Miaosheng Li, Morgantown, WV (US)

(73) Assignee: Protea Biosciences, Inc., Morgantown, WV (US)

(*) Notice: Subject to any disclaimer, the term of this patent is extended or adjusted under 35 U.S.C. 154(b) by 0 days.

(21) Appl. No.: 13/532,137

(22) Filed: Jun. 25, 2012

(65) Prior Publication Data

US 2012/0264157 A1  Oct. 18, 2012

Related U.S. Application Data

(60) Continuation of application No. 13/195,809, filed on Aug. 1, 2011, now Pat. No. 8,232,423, which is a division of application No. 12/454,742, filed on May 22, 2009, now Pat. No. 8,013,179.

(60) Provisional application No. 61/055,746, filed on May 23, 2008.

(51) Int. Cl.
*C12Q 1/37* (2006.01)
*C12P 21/06* (2006.01)
*C07K 1/02* (2006.01)
*B01D 57/02* (2006.01)

(52) U.S. Cl.
USPC ............ 435/23; 435/68.1; 530/368; 530/408; 530/412; 204/451; 204/456

(58) Field of Classification Search .................. None
See application file for complete search history.

(56) References Cited

U.S. PATENT DOCUMENTS

| | | | |
|---|---|---|---|
| 3,023,182 | A | 2/1962 | Tanabe et al. |
| 4,301,044 | A | 11/1981 | Wentler et al. |
| 5,093,043 | A | 3/1992 | Jakobson et al. |
| 5,264,460 | A | 11/1993 | Jakobson et al. |
| 6,429,200 | B1 | 8/2002 | Monahan et al. |
| 7,022,861 | B1 | 4/2006 | McElhanon et al. |
| 7,074,936 | B2 | 7/2006 | Caprioli et al. |
| 7,091,041 | B2 | 8/2006 | Monahan et al. |
| 7,229,539 | B1 | 6/2007 | Lee et al. |
| 7,351,837 | B1 | 4/2008 | McElhanon et al. |
| 8,013,179 | B2 | 9/2011 | Powell et al. |
| 2004/0152913 | A1 | 8/2004 | Caprioli et al. |
| 2006/0240562 | A1 | 10/2006 | Caprioli et al. |
| 2006/0270584 | A1 | 11/2006 | Frantz et al. |
| 2011/0282096 | A1 | 11/2011 | Powell et al. |

FOREIGN PATENT DOCUMENTS

| | | |
|---|---|---|
| WO | WO 02/097393 A1 | 12/2002 |
| WO | WO 03/106379 A1 | 12/2003 |

OTHER PUBLICATIONS

F.L. Van Delft et al., A Sulfitylation-Oxidation Protocol for the Preparation of Sulfates. *J. Org. Chem.*, 2006, 71, 7473-7476.
T. Takeda et al., Synthesis and Properties of Soap Types of Double-Chain Cleavable Surfactants Derived from Pyruvate. *J. Oleo Sci.*, 2004, 53 (2), 89-95.
M. Fung et al., Hybrid Surfactants Containing Separate Hydrocarbon and Fluorocarbon Chains. *J. Phys. Chem.*, 1992, 96, 6738-6742.
M. Iver et al., Synthesis of pH-Degradable Nonionic Surfactants and Their Applications in Microemulsions. *Langmuir* 2001, 17, (22), 6816-6821.
D.A. Jaeger et al., Preparation and Characterization of Glycerol-Based Cleavable Surfactants and Derived Vesicles, *J. Am. Chem. Soc.* 1989, 111, (8), 3001-3006.
D.A. Jaeger et al., Acid-Catalyzed Hydrolysis and Monolayer Properties of Ketal-Based Cleavable Surfactants. *Langmuir* 1990, 6, (3), 547-554.
D.A. Jaeger et al., Cleavable Quaternary Hydrazinium Surfactants. *Langmuir* 1998, 14, (7), 1940-1941.
B. Guyot, et al., Esterification of phenolic acids from green coffee with an immobilized lipase from *Candida antarctica* in solvent-free medium. *Biotechnology Letters*. Jun. 1997, vol. 19, (6), 529-532.
R.M. Caprioli et al., Mass Spectrometry of Intracellular and Membrane Proteins Using Cleavable Detergents. *Anal. Chem.* 2003, 75, 6642-6647.
Eckert and Liotta, "Designing Smart Surfactants" printed from www.chbe.gatech.edu/eckert/pdf/_surfactant.pdf, Internet site accessed on Dec. 22, 2009, 8 pages.
"Remove detergent from protein samples", printed from www.thermo.com/eThermo/CMA/PDFs/.../articlesFile_6580.pdf, Internet site accessed on Dec. 22, 2009, 2 pages.
"Care and Use Manual" printed from http://www.waters.com/waters/support.htm?locale=en_NG&lid=10008439&cid=511442&type=USRM, Internet site accessed on Dec. 22, 2009, 4 pages.
ProteasMAX™ Surfactant, Trypsin Enhancer, printed from www.promega.com/tbs/tb373/tb373.pdf, Internet site accessed on Dec. 22, 2009, 20 pages.

(Continued)

*Primary Examiner* — Rebecca Anderson
*Assistant Examiner* — Alicia L Otton
(74) *Attorney, Agent, or Firm* — K&L Gates LLP

(57) ABSTRACT

Anionic acid-labile surfactants may generally comprise compounds represented by the formula:

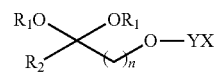

wherein $R_1$ is independently selected from —$(CH_2)_{0-9}CH_3$, $R_2$ is selected from the group consisting of —H and —$(CH_2)_{0-5}CH_3$, Y is an anion, X is a cation, and n is an integer from 1 to 8. Methods of making and using the anionic acid-labile surfactants are also described. The anionic acid-labile surfactants may be used to facilitate the solubilization of proteins and other molecules in an aqueous environment.

20 Claims, 3 Drawing Sheets

OTHER PUBLICATIONS

PPS Silent® Surfactant, Acid Cleavable Detergent, Use and Storage Instructions, printed from www.proteindiscovery.com/_downloads/PPS_PI_UseAndStorage.pdf, Internet site accessed on Dec. 22, 2009, 1 page.

FAQs about PPS Silent® Surfactant, printed from http://www.proteindiscovery.com/pages/support/faq_pps.html, Internet site accessed on Dec. 22, 2009, 2 pages.

RapiGest™ SF, printed from www.orbital.com.cn/up/Waters%20Life%20Science%20Solutions.pdf, Internet site accessed on Dec. 22, 2009, 1 page.

McMillen et al., "Identifying Regions of Membrane Proteins in Contact with Phospholipid Head Groups: Covalent Attachment of a New Class of Aldehyde Lipid Labels to Cytochrome $c$ Oxidase", Biochemistry, 1986, (25) 182-193.

Rouhana et al., "Aggregation-Resistant Water-Soluble Gold Nanoparticles", Langmuir, 2007 (23) 12799-12801.

FIG. 2

| Protein / Surfactant | PMF Mascot Score | Sequence Coverage | No. of mass values matched | No. of mass values searched |
|---|---|---|---|---|
| Proteasmax BSA (a) | 28 | 9 | 5 | 19 |
| Proteasmax BSA (b) | 33 | 9 | 5 | 14 |
| Proteasmax BSA (c) | 52 | 11 | 6 | 11 |
| Average | 38 | | | |
| Rapigest BSA (a) | 36 | 15 | 10 | 51 |
| Rapigest BSA (b) | 35 | 15 | 10 | 53 |
| Rapigest BSA (c) | 92 | 26 | 16 | 48 |
| Average | 54 | | | |
| PPS BSA (a) | no I.D | | | |
| PPS BSA (b) | no I.D | | | |
| PPS BSA (c) | no I.D | | | |
| AALS6 BSA (a) | 84 | 23 | 14 | 41 |
| AALS6 BSA (b) | 108 | 23 | 16 | 39 |
| AALS6 BSA (c) | 86 | 23 | 15 | 44 |
| Average | 93 | | | |
| BSA - Control | 92 | 25 | 17 | 56 |

FIG. 3

| Protein / Surfactant | MS/MS Mascot Ion Score | No. of peptide Sequences matched |
|---|---|---|
| Proteasmax Ovalbumin (a) | 257 | 3 |
| Proteasmax Ovalbumin (b) | 375 | 4 |
| Proteasmax Ovalbumin (c) | 355 | 4 |
| Average | 329 | |
| | | |
| Rapigest Ovalbumin (a) | 364 | 4 |
| RapigestOvalbumin (b) | 302 | 3 |
| Rapigest Ovalbumin (c) | 357 | 4 |
| Average | 341 | |
| | | |
| PPS Ovalbumin (a) | 166 | 2 |
| PPS Ovalbumin (b) | no I.D | |
| PPS Ovalbumin (c) | no I.D | |
| Average | 166 | |
| | | |
| AALS6 Ovalbumin (a) | 380 | 5 |
| AALS6 Ovalbumin (b) | 550 | 6 |
| AALS6 Ovalbumin (c) | 531 | 6 |
| Average | 487 | |
| | | |
| Ovalbumin_Control | 347 | 3 |

ANIONIC ACID-LABILE SURFACTANTS AND METHODS OF USE

CROSS-REFERENCE TO RELATED APPLICATIONS

This application is a continuation of U.S. application Ser. No. 13/195,809, filed on Aug. 1, 2011, now U.S. Pat. No. 8,232,423, which is a divisional of U.S. application Ser. No. 12/454,742, filed on May 22, 2009, now U.S. Pat. No. 8,013,179, which claims the benefit of U.S. Provisional Application No. 61/055,746, filed on May 23, 2008. Each of the foregoing applications is incorporated herein by reference in its entirety.

BACKGROUND

The compounds and methods described herein generally relate to anionic acid-labile surfactants and methods of use.

Proteomics is the study of the structure and function of proteins and other molecules in biological systems. Some purification and identification techniques used in proteomics require the proteins and other molecules to be solubilized in an aqueous environment. Most proteins and other hydrophobic molecules or molecules with significant hydrophobic regions, however, are not readily soluble in an aqueous environment. A surfactant or detergent may generally be used to facilitate the solubilization of proteins and other molecules in an aqueous environment.

Ionic cleavable surfactants have been successfully used to facilitate the solubilization of proteins and other molecules in an aqueous environment. Ionic cleavable surfactants may generally comprise a polar (hydrophilic) group joined by a cleavable linker to a non-polar (hydrophobic) group. The ionic cleavable surfactant may be cleaved or degraded by utilizing acidic conditions, basic conditions, photodegradation, thermal degradation, or chemical reduction. The cleavage by-products may be separated from the proteins or other molecules using standard isolation techniques. Conventional ionic cleavable surfactants, however, may generally comprise chemical structures that are complex to synthesize, require harsh conditions (e.g., pH 1-2) or long periods of time (up to several hours) to cleave, and/or generate cleavage by-products that interfere with purification and identification techniques.

Accordingly, more efficient ionic cleavable surfactants and methods of use are desirable.

SUMMARY

According to certain embodiments, more efficient ionic cleavable surfactants and methods of use are described.

In certain embodiments, anionic acid-labile surfactants may generally comprise a compound of the formula:

$$\begin{array}{c} R_1O \quad OR_1 \\ \diagdown \diagup \\ R_2 \diagup \diagdown (\phantom{X})_n \end{array} O-YX$$

wherein $R_1$ is independently selected from $-(CH_2)_{0-9}CH_3$, $R_2$ is selected from the group consisting of $-H$ and $-(CH_2)_{0-5}CH_3$, Y is an anion, X is a cation, and n is an integer from 1 to 8.

In certain embodiments, methods of using the anionic acid-labile surfactants may generally comprise adjusting a sample to pH 6-12; mixing a solvent with at least one of the anionic acid-labile surfactants; contacting the sample with the mixture; and cleaving the at least one anionic acid-labile surfactant.

DESCRIPTION OF THE DRAWINGS

The various non-limiting embodiments of anionic acid-labile surfactants and methods of use described herein may be better understood by considering the following description in conjunction with the accompanying drawings.

FIG. 2 illustrates the protein score from in-solution digestion of BSA of an embodiment of an anionic acid-labile surfactant and three conventional anionic acid-labile surfactants.

FIG. 3 illustrates the protein score from in-solution digestion of ovalbumin of an embodiment of an anionic acid-labile surfactant and three conventional anionic acid-labile surfactants.

DESCRIPTION OF CERTAIN EMBODIMENTS

A. Definitions

Figure 1:
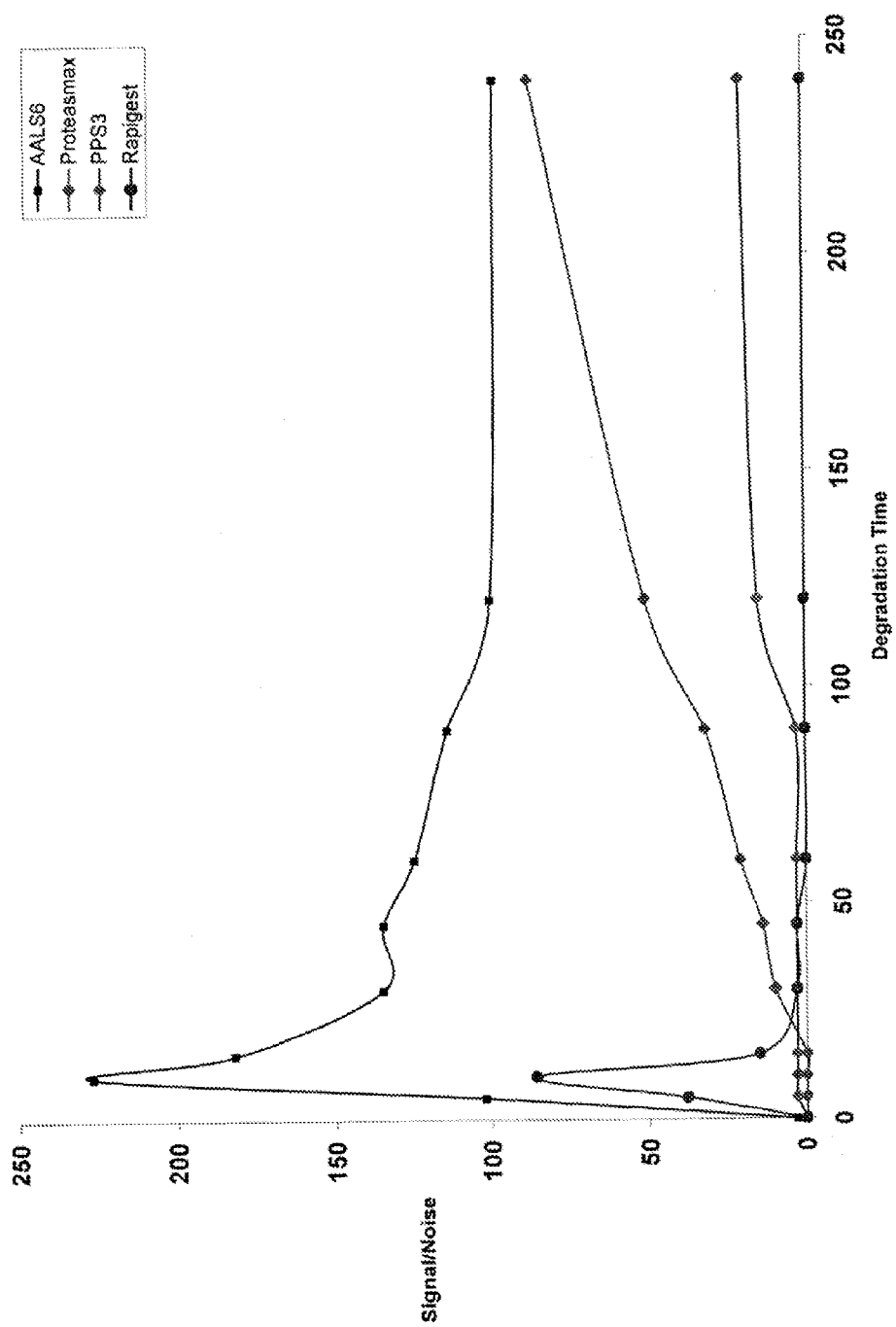
FIG. 1 illustrates the degradation time of an embodiment of an anionic acid-labile surfactant and three conventional anionic acid-labile surfactants.

As generally used herein, the term "comprising" refers to various components conjointly employed in the manufacture and use of the compounds and methods described herein. Accordingly, the terms "consisting essentially of" and "consisting of" are embodied in the term "comprising".

As generally used herein, the grammatical articles including "one", "a", "an", and "the" refer to "at least one" or "one or more" of what is claimed or described, unless otherwise indicated. Thus, the articles are used herein to refer to one or more than one (i.e., to at least one) of the grammatical objects of the article. By way of example, "a component" means one or more components, and thus, possibly, more than one component is contemplated and may be employed or used.

As generally used herein, the terms "include", "includes" and "including" are meant to be non-limiting.

As generally used herein, the terms "have", "has" and "having" are meant to be non-limiting.

All numerical quantities or characteristics stated herein are approximate unless otherwise indicated, meaning that all numerical quantities are to be understood as being prefaced and modified in all instances by the term "about". Each numerical quantity is intended to mean both the recited value and a functionally equivalent range surrounding that value unless otherwise indicated. At the very least, and not as an attempt to limit the application of the doctrine of equivalents to the scope of the claims, each numerical parameter described in the present description should at least be construed in light of the number of reported significant digits and by applying ordinary rounding techniques. Notwithstanding the approximations of numerical quantities stated herein, the numerical quantities described in the Examples are reported as precisely as possible.

All numerical ranges stated herein include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10. Any maximum numerical limitation recited herein is intended to include all lower numerical limitations. Any minimum numerical limitation recited herein is intended to include all higher numerical limitations. Accordingly, Applicant(s)

reserves the right to amend the present disclosure, including the claims, to expressly recite any sub-range subsumed within the ranges expressly recited herein. All such ranges are intended to be inherently disclosed herein such that amending to expressly recite any such sub-ranges would comply with the requirements of 35 U.S.C. §112, first paragraph, and 35 U.S.C. §132(a).

As generally used herein, the terms "detergent" and "surfactant" refer to compounds and compositions that may facilitate the solubilization of proteins, other hydrophobic molecules, or molecules with significant hydrophobic regions in an aqueous environment.

As generally used herein, the term "cleave" refers to reducing or destroying the detergent properties of the surfactant. In at least one embodiment, the term "cleave" refers to separating the cleavable linker and the polar group and/or non-polar groups. In at least one embodiment, the term "cleave" refers to degrading or disrupting the bond between the cleavable linker and the polar group and/or non-polar groups.

As generally used herein, the term "labile" refers to the property of a molecule or bond to undergo chemical, physical, or biological change, degradation, or disruption.

As generally used herein, the term "sample-surfactant complex" refers to the molecular complex that may be formed by a surfactant and a sample.

As generally used herein, the term "sample" refers to any molecule that may be used with the anionic acid-labile surfactants or methods described herein, such as, for example, but not limited to, hydrophobic molecules, molecules with significant hydrophobic regions, proteins, peptides, polypeptides, polymers, nucleic acids, lipids, lipophillic cellular components, hydrophilic extracellular components, and any combinations thereof.

As generally used herein, when any variable occurs more than one time in a chemical formula, its definition on each occurrence is independent of its definition at every other occurrence.

As generally used herein, a dash ("-") that is not between two letters or symbols is used to indicate a point of attachment for a substituent.

As generally used herein, the term "alkyl" refers to saturated aliphatic groups, including straight-chain alkyl, branched-chain alkyl, straight or branched chain heteroalkyl, cycloalkyl, heterocyclic alkyl, alkyl substituted cycloalkyl groups, and cycloalkyl substituted alkyl groups, including, for example, but not limited to, methyl, ethyl, n-propyl, isopropyl, n-butyl, sec-butyl, t-butyl, pentyl, n-hexyl, and cyclohexyl.

As generally used herein, the notation "n" in reference to an organic group, wherein n is an integer or an integer range, indicates that the group may contain n carbon atoms or that range of carbon atoms per group. The terminology "$C_n$-$C_m$" in reference to an organic group, wherein n and m are each integers, indicates that the group may contain from n carbon atoms to m carbon atoms per group.

Unless otherwise indicated, all compound or composition levels refer to the active portion of that compound or composition, and are exclusive of impurities, for example, residual solvents or by-products, which may be present in commercially available sources of any compounds or compositions.

All percentages and ratios are calculated by weight unless otherwise indicated. All percentages and ratios are calculated based on the total weight of the compound or composition unless otherwise indicated.

This disclosure describes various elements, features, aspects, and advantages of various non-limiting embodiments of anionic acid-labile surfactants and methods of use. It is to be understood that certain descriptions of the disclosed embodiments have been simplified to illustrate only those elements, features and aspects that are relevant to a clear understanding of the disclosed embodiments, while eliminating, for purposes of clarity, other elements, features and aspects. Persons having ordinary skill in the art, upon considering the present description of the disclosed embodiments, will recognize that various combinations or sub-combinations of the disclosed embodiments and other elements, features, and/or aspects may be desirable in a particular implementation or application of the disclosed embodiments. However, because such other elements and/or features may be readily ascertained by persons having ordinary skill upon considering the present description of the disclosed embodiments, and are not necessary for a complete understanding of the disclosed embodiments, a description of such elements and/or features is not provided herein. As such, it is to be understood that the description set forth herein is merely exemplary and illustrative of the disclosed embodiments and is not intended to limit the scope of the invention as defined solely by the claims.

B. Overview

In certain embodiments, the ionic acid-labile surfactants may generally comprise a non-polar (hydrophobic) group joined by a cleavable linker to a polar (hydrophilic) group. In certain embodiments, the anionic acid-labile surfactants described herein may comprise two shorter chain hydrophobic tails that individually bind weaker than conventional surfactants, but collectively bind nearly as well. In at least one embodiment, the interaction between the cleavable linker and the polar group and/or non-polar group may be covalent bonding, ionic bonding, hydrogen bonding, or van der Waals bonding. In at least one embodiment, the ionic acid-labile surfactant may be cleavable. In at least one embodiment, the ionic acid-labile surfactant may be labile. In at least one embodiment, the ionic acid-labile surfactant may be acid cleavable, i.e., acidic conditions may be used to cleave the bond between the cleavable linker and the polar group and/or non-polar groups. In at least one embodiment, the ionic acid-labile surfactant may be acid cleavable with the proviso that the acid is not a strong acid.

In at least one embodiment, the ionic acid-labile surfactants may be hydrolyzed at a relatively low pH to generate cleavage by-products, including an ionic, water-soluble or partially water-soluble compound (e.g., an anionic head group) and a neutral, water-soluble or partially water-soluble compound (e.g., short to mid-length alcohols, such as pentanol, hexanol, heptanol, and octanol). These cleavage by-products may be removed from the sample-surfactant complex more readily than the original surfactants because they exhibit reduced, if any, detergent characteristics and/or do not readily bind to the sample. In at least one embodiment, the cleavage by-products may be washed away by utilizing a solid phase extraction step in which the sample may be bound to the surface of a reversed phase chromatographic bead.

In at least one embodiment, the polar group and/or non-polar groups may improve the formation of a surfactant-sample complex. In at least one embodiment, the polar group and/or non-polar groups may improve the solubility of the cleavage by-products. In at least one embodiment, the cleavage by-products may minimize signal suppression. In at least one embodiment, the cleavage by-products may have reduced or negligible detergent characteristics. In at least one embodiment, the cleavage by-products may be removable by standard isolation techniques. In at least one embodiment, fewer adducts of the sample and non-degraded surfactant may be formed.

The anionic acid-labile surfactants described herein may be especially useful for purification and identification techniques in which conventional cleavage by-products interfere with the purification and identification of the sample. Examples of proteomic purification and identification technologies that may benefit from the anionic acid-labile surfactants described herein include, but are not limited to, ion-pair liquid chromatography, liquid chromatography, mass spectrometric detection, liquid-liquid extraction, solid phase extraction, cell lysis, and other technologies that may benefit from the removal of the surfactants after use.

C. Anionic Acid-Labile Surfactants

In certain embodiments, the ionic acid-cleavable surfactant may generally comprise an anionic acid-cleavable surfactant comprising at least one non-polar group selected from the group consisting of hydrogen, $C_1$-$C_{12}$ alkyl, and substituted $C_1$-$C_{12}$ alkyl; a polar group comprising an anionic group; and a cleavable linker comprising a ketal or an acetal.

In certain embodiments, the anionic acid-cleavable surfactant may generally comprise a compound of Formula I or a compound of Formula II:

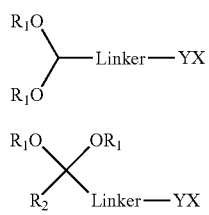

Formula I

Formula II wherein $R_1$ may be independently selected from the group consisting of hydrogen, $C_1$-$C_{12}$ alkyl, substituted $C_1$-$C_{12}$ alkyl, $R_2$ may be selected from the group consisting of hydrogen, $C_1$-$C_{12}$ alkyl, substituted $C_1$-$C_{12}$ alkyl, Linker may be selected from the group consisting of $C_1$-$C_{12}$ alkyl and substituted $C_1$-$C_{12}$ alkyl, X may be a cation, and Y may be an anion. In at least one embodiment, X may be selected from the group consisting of sodium, potassium, lithium, ammonium, and calcium ions. In at least one embodiment, Y may comprise a hard anionic charge selected from the group consisting of sulfate, sulfonate, phosphate, phosphonate and borate ions. In at least one embodiment, Y may comprise a weak anionic charge selected from the group consisting of carbonate, acetate, and formate ions.

In at least one embodiment, the $R_1$ substituted $C_1$-$C_{12}$ alkyl may be selected from the group consisting of halogen substitution (e.g., —F, —Cl, —Br, or —I substitution), heterocyclic substitution, cyclic alkyl substitution, amide substitution, amine substitution, ester substitution, ether substitution, and phenyl substitution. In at least one embodiment, $R_1$ substituted $C_1$-$C_{12}$ alkyl may be at least one of fluoralkyl substitution, pre-fluoroalkyl substitution, and benzene substitution.

In at least one embodiment, the $R_2$ substituted $C_1$-$C_{12}$ alkyl may be selected from the group consisting of alkoxy substitution and halogen substitution (e.g., —F, —Cl, —Br, or —I substitution). In at least one embodiment, $R_2$ substituted $C_1$-$C_{12}$ alkyl may be at least one of fluoralkyl substitution and pre-fluoroalkyl substitution.

In at least one embodiment, the Linker substituted $C_1$-$C_{12}$ alkyl may be selected from the group consisting of halogen substitution (e.g., —F, —Cl, —Br, or —I substitution), heterocyclic substitution, cyclic alkyl substitution, amide substitution, amine substitution, ester substitution, ether substitution, and phenyl substitution. In at least one embodiment, Linker substituted $C_1$-$C_{12}$ alkyl may be at least one of fluoralkyl substitution, pre-fluoroalkyl substitution, and benzene substitution.

In certain embodiments, anionic acid-labile surfactants may generally comprise a compound represented by Formula III or a compound represented by Formula IV:

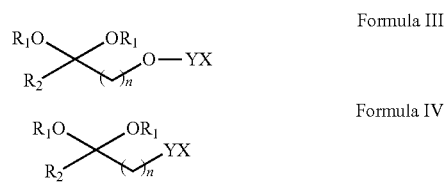

Formula III

Formula IV wherein $R_1$ may be independently selected from the group consisting of $C_1$-$C_{12}$ alkyl and substituted $C_1$-$C_{12}$ alkyl, $R_2$ may be selected from the group consisting of hydrogen, $C_1$-$C_{12}$ alkyl, substituted $C_1$-$C_{12}$ alkyl, X may be a cation, Y may be an anion, and n may be an integer from 1 to 12. In at least one embodiment, $R_1$ may be independently selected from —$(CH_2)_{0-9}CH_3$, $R_2$ may be selected from the group consisting of —H and —$(CH_2)_{0-5}CH_3$, Y may be selected from the group consisting of —$SO_3^-$ and —$PO_3^-$, X may be a cation, and n may be an integer from 1 to 8. In at least one embodiment, $R_1$ may be independently selected from —$(CH_2)_{0-9}CH_3$, with the proviso that $R_1$ does not comprise a branched-chain alkyl group or a cycloalkyl group. In at least one embodiment, $R_1$ may be independently a saturated, straight-chain $C_1$-$C_{12}$ alkyl group. In at least one embodiment, X may be selected from the group consisting of sodium, potassium, lithium, and ammonium ions.

In certain embodiments, anionic acid-labile surfactants may generally comprise a compound represented by Formula V or compound represented by Formula VI

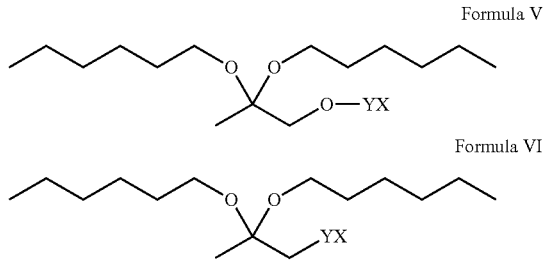

Formula V

Formula VI wherein X may be a cation and Y may be an anion. In at least one embodiment, X may be selected from the group consisting of sodium, potassium, lithium, and ammonium ions. In at least one embodiment, Y may be selected from the group consisting of —$SO_3^-$ and —$PO_3^-$. In at least one embodiment, the anionic acid-labile surfactant may comprise sodium 2,2-bis(hexyloxy)propyl sulfonate. In at least one embodiment, the anionic acid-labile surfactant may comprise sodium 2,2-bis(hexyloxy)propyl sulfate.

In certain embodiments, anionic acid-labile surfactants may generally comprise a compound represented by Formula VII or compound represented by Formula VIII

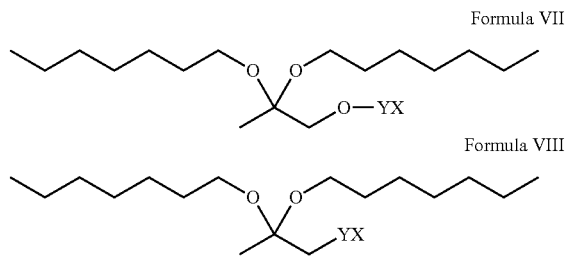

Formula VII

Formula VIII wherein X may be a cation and Y may be an anion. In at least one embodiment, X may be selected from the group consisting of sodium, potassium, lithium, and ammonium ions. In at least one embodiment, Y may be selected from the group consisting of $—SO_3^-$ and $—PO_3^-$. In at least one embodiment, the anionic acid-labile surfactant may comprise sodium 2,2-bis(heptyloxy)propyl sulfonate. In at least one embodiment, the anionic acid-labile surfactant may comprise sodium 2,2-bis(heptyloxy)propyl sulfate.

In certain embodiments, anionic acid-labile surfactants may generally comprise a compound represented by Formula III or compound represented by Formula IV having a rate of degradation of less than 30 minutes. In at least one embodiment, the rate of degradation may be 4-24 minutes. In at least one embodiment, the rate of degradation may be 6-12 minutes. In at least one embodiment, the rate of degradation may be 10 minutes. The rate of degradation relates to the rate of how easily the surfactant degrades. Without wishing to be bound to any particular theory, the rate of degradation may depend on the stability of the sample-surfactant complex. The stability of the sample-surfactant complex may depend on the chemical structure of the surfactant and/or the chemical structure of the sample-surfactant complex. For example, the rate of degradation may depend on the electron donating groups and/or electron withdrawing groups.

In certain embodiments, a composition may comprise a sample-surfactant complex. In at least one embodiment, the sample-surfactant complex may generally comprise a sample and an anionic acid-labile surfactant according to Formula III or Formula IV. In at least one embodiment, the composition may comprise an anionic acid-labile surfactant according to Formula III or Formula IV and a protein mixture for electrophoresis. Without wishing to be bound to any particular theory, in solution, the hydrophobic tails of the surfactants may associate with the hydrophobic portion of the sample, e.g., proteins, via hydrophobic interactions. The hydrophilic heads of the surfactants may align outwardly from the hydrophobic tails to maximize the distance between the two opposing chemistries, and toward the bulk aqueous solvent where the hydrophilic heads may associate with the polar water molecules. In at least one embodiment, the sample-surfactant complex may improve the solubility of the native (uncomplexed) sample. In at least one embodiment, the sample-complex may improve the solubility of the native sample in that the hydrophilic heads provide a cumulative improvement in the soluble nature of the sample-surfactant complex. In at least one embodiment, the sample-surfactant complex may provide an increased potential for solvation and maintenance of a dissolved state.

D. Synthesis of Certain Embodiments

The synthesis of the anionic acid-labile surfactant compounds may be carried out using commercially available starting materials and known chemical reaction steps. For example, synthetic methods for the preparation of various surfactant compounds may be described in Huibers, M.; Manuzi, A.; Rutjes, F.; Delft, F. J. Org. Chem., 2006, 71, 7473-7476; Ono, D.; Yamamura, S.; Nakamura, M.; Takeda, T. J. Ole. Sci., 2004, 53 (2), 89-95; and Guo, W.; Li, Z.; Fung, B. M. J. Phys. Chem., 1992, 96, 6738-6742. The methods of synthesizing the anionic acid-labile surfactants may produce isomers. Although the methods of using the anionic acid-labile surfactants may not require separation of these isomers, such separation may be accomplished, if desired, by standard separation methods, such as, for example, preparative high performance liquid chromatography.

The following examples for the preparation of anionic acid-labile surfactants are for illustrative purposes, and not intended to limit the scope of the anionic acid-labile surfactants compounds and methods described herein. Additionally, in practicing the anionic acid-labile surfactants and methods, one of ordinary skill in the art would understand that various modifications to the following procedures would be routine, in light of the teachings herein, and that such modifications would be within the spirit and scope of the anionic acid-labile surfactants compounds and methods described herein.

1. Preparation of sodium 2,2-bis(hexyloxy)propyl sulfate $^1$H NMR and $^{13}$C NMR spectra are recorded on a Varian 600 MHz spectrometer. Chemical shifts are reported relative to $CDCl_3$ ($\delta$ 7.24 ppm) or $C_6D_6$ ($\delta$ 7.16 ppm) for $^1$H NMR and $CDCl_3$ ($\delta$ 77.0 ppm) or $C_6D_6$ ($\delta$ 128.4 ppm) for $^{13}$C NMR Infrared (IR) spectra are obtained on a FT-IR spectrometer. Sorbtech 60A (230-400 mesh) silica gel is used for flash chromatography. Analytical thin-layer chromatography is performed with precoated glass-backed plates (K6F 60 Å, F254) and visualized by quenching of fluorescence and by charring after treatment with p-anisaldehyde or phosphomolybdic acid or potassium permanganate stain. $R_f$ values are obtained by elution in the stated solvent ratios (v/v). Ether ($Et_2O$), methylene chloride ($CH_2Cl_2$) and toluene are dried by passing through an activated alumina (8×14 mesh) column with argon gas pressure. Commercial reagents are purchased from Fisher Scientific or Sigma-Aldrich and used without purification unless otherwise noted. Air and/or moisture-sensitive reactions are carried out under an atmosphere of argon/nitrogen using oven/flamed-dried glassware and standard syringe/septa techniques.

a. Synthesis of hexyl 2,2-bis(hexyloxy)propanoate

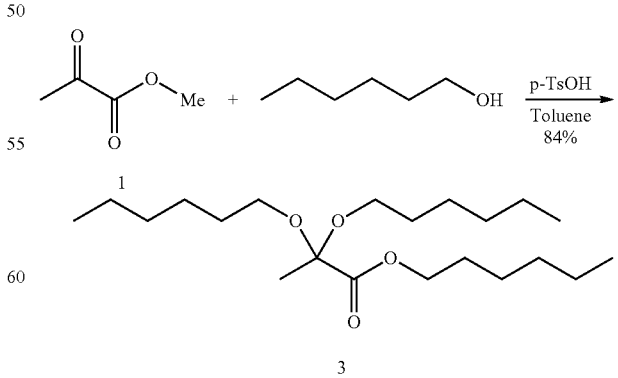

To a solution of methyl pyruvate 1 (10.0 g, 98.0 mmol) in toluene (100 mL) is added 1-hexanol 2 (40.1 g, 392 mmol)

and p-TsOH (186 mg, 0.98 mmol). The mixture is heated to reflux for 10 hours with azeotropic removal of water from the reaction mixture. The reaction is quenched with saturated NaHCO$_3$ (100 mL), and the reaction mixture is extracted with ethyl acetate (2×100 mL). The combined organic layers are washed with brine (100 mL) and dried over anhydrous sodium sulfate. The solvent is removed and the residue is purified by silica gel chromatography (1→10% ethyl acetate/hexane) to give hexyl 2,2-bis(hexyloxy)propanoate 3 (29.5 g, 84%) as a colorless oil: R$_f$ (15% EtOAc/hexane)=0.53; IR (thin film, cm$^{-1}$) 2956, 2930, 2860, 1746 (C=O), 1467, 1280, 1137, 1062. $^1$H NMR (600 MHz, CDCl$_3$) δ 4.14 (t, J=7.2 Hz, 2H), 3.48 (ddd, J=9.0, 7.2, 6.6 Hz, 2H), 3.35 (ddd, J=9.0, 7.2, 6.6 Hz, 2H), 1.65-1.63 (m, 2H), 1.59-1.54 (m, 4H), 1.49 (s, 3H), 1.35-1.24 (m, 18H), 0.86 (t, J=7.2 Hz, 9H); $^{13}$C NMR (150 MHz, CDCl$_3$) δ 170.2, 99.5, 65.4, 62.6, 31.7, 31.3, 29.7, 28.5, 25.8, 25.5, 22.6, 22.5, 21.9, 14.0, 13.9.

b. Synthesis of 2,2-bis(hexyloxy)propan-1-ol

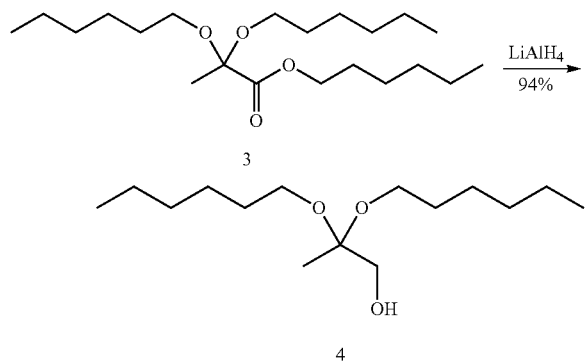

To a mixture of LiAlH$_4$ (3.44 g, 90.5 mmol) in Et$_2$O (200 mL) is added a solution of ester 3 (29.5 g, 82.3 mmol) in Et$_2$O (100 mL). After addition, the mixture is refluxed for 6 hours. The reaction mixture is cooled to 0° C. and quenched with ethyl acetate (20 mL) and H$_2$O (20 mL). The mixture is added to saturated potassium sodium tartrate (300 mL) and stirred at 23° C. for 12 hours. The mixture is extracted with Et$_2$O (2×200 mL) and the combined organic layers are dried over anhydrous sodium sulfate. The solvent is removed and the residue is purified by silica gel chromatography (1→10% ethyl acetate/hexane) to give 2,2-bis(hexyloxy)propan-1-ol 4 (20.6 g, 94%) as a colorless oil: R$_f$ (15% EtOAc/hexane)= 0.20; IR (thin film, cm$^{-1}$) 3430, 2955, 2929, 2859, 1467, 1378, 1244, 1155, 1112, 1064, 876; $^1$H NMR (600 MHz, C$_6$D$_6$) δ 3.58 (d, J=6.6 Hz, 2H), 3.43 (t, J=6.6 Hz, 4H), 1.58 (t, J=6.6 Hz, 1H), 1.53 (m, 4H), 1.36 (s, 3H), 1.34-1.22 (m, 12H), 0.88 (t, J=7.2 Hz, 6H); $^{13}$C NMR (150 MHz, C$_6$D$_6$) δ 101.0, 66.2, 61.3, 32.5, 30.9, 26.8, 23.4, 21.3, 14.6.

c. Synthesis of sodium 2,2-bis(hexyloxy)propyl sulfate

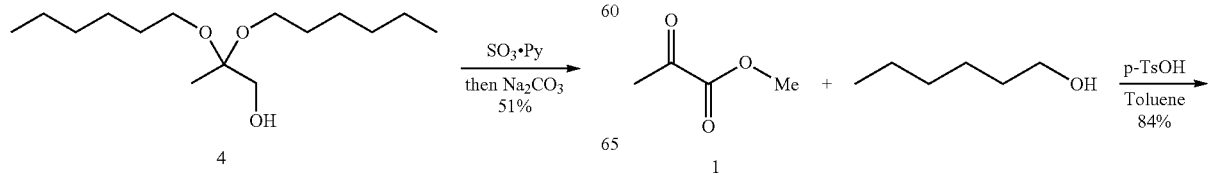

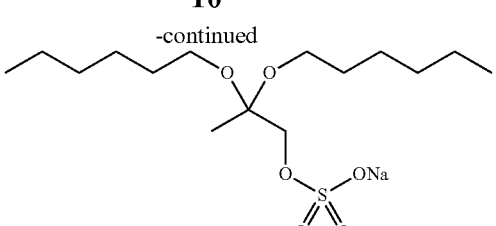

To a solution of alcohol (2.50 g, 9.60 mmol) in pyridine (5 mL) is added SO$_3$.Py (2.29 g, 14.4 mmol). The reaction mixture is stirred at 80° C. for 10 hours. The reaction mixture is cooled to 23° C. and quenched by pouring the mixture into an ice-cooled sodium carbonate solution (10 g in 20 mL of water). The mixture is extracted with butanol (2×50 mL). The combined organic layers are washed with brine and dried over anhydrous sodium sulfate. The solvent is removed and the residue is purified by silica gel chromatography (10→100% ethyl acetate/hexane) to give sodium 2,2-bis(hexyloxy)propanyl ethyl sulfate 5 (4.07 g, 74%) as a colorless solid: R$_f$ (20% EtOH/EtOAc)=0.48; IR (thin film, cm$^{-1}$) 3506, 2956, 2930, 2056, 1642, 1467, 1380, 1228, 1015, 820; $^1$H NMR (600 MHz, CDCl$_3$) δ 3.99 (s, 2H), 3.42 (t, J=7.2 Hz, 4H), 1.51-1.49 (m, 4H), 1.36 (s, 3H), 1.30-1.24 (m, 12H), 0.86 (t, J=7.2 Hz, 6H); $^{13}$C NMR (150 MHz, CDCl$_3$) δ 99.2, 69.8, 60.8, 31.8, 29.8, 25.9, 22.7, 20.8, 14.0.

2. Preparation of sodium 2,2-bis(hexyloxy)propyl sulfate $^1$H NMR and $^{13}$C NMR spectra are recorded on a Varian 600 MHz spectrometer. Chemical shifts are reported relative to CDCl$_3$ (δ 7.24 ppm) or C$_6$D$_6$ (δ 7.16 ppm) for $^1$H NMR and CDCl$_3$ (δ 77.0 ppm) or C$_6$D$_6$ (δ 128.4 ppm) for $^{13}$C NMR. Infrared (IR) spectra are obtained on a FT-IR spectrometer. Sorbtech 60A (230-400 mesh) silica gel is used for flash chromatography. Analytical thin-layer chromatography is performed with precoated glass-backed plates (K6F 60 Å, F254) and visualized by quenching of fluorescence and by charring after treatment with p-anisaldehyde or phosphomolybdic acid or potassium permanganate stain. R$_f$ values are obtained by elution in the stated solvent ratios (v/v). Ether (Et$_2$O), methylene chloride (CH$_2$Cl$_2$) and toluene are dried by passing through an activated alumina (8×14 mesh) column with argon gas pressure. Commercial reagents are purchased from Fisher Scientific or Sigma-Aldrich and used without purification unless otherwise noted. Air and/or moisture-sensitive reactions are carried out under an atmosphere of argon/nitrogen using oven/flamed-dried glassware and standard syringe/septa techniques.

a. Synthesis of hexyl 2,2-bis(hexyloxy)propanoate

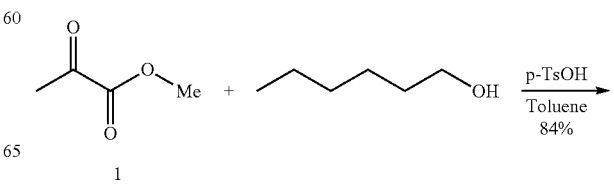

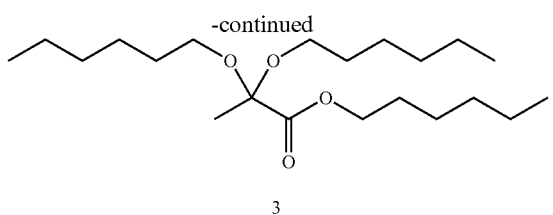

3

To a solution of methyl pyruvate 1 (10.0 g, 98.0 mmol) in toluene (100 mL) is added 1-hexanol 2 (40.1 g, 392 mmol) and p-TsOH (186 mg, 0.98 mmol). The mixture is heated to reflux for 10 hours with azeotropic removal of water from the reaction mixture. The reaction is quenched with saturated $NaHCO_3$ (100 mL), and the reaction mixture is extracted with ethyl acetate (2×100 mL). The combined organic layers are washed with brine (100 mL) and dried over anhydrous sodium sulfate. The solvent is removed and the residue is purified by silica gel chromatography (1→10% ethyl acetate/hexane) to give hexyl 2,2-bis(hexyloxy)propanoate 3 (29.5 g, 84%) as a colorless oil: $R_f$ (15% EtOAc/hexane)=0.53; IR (thin film, $cm^{-1}$) 2956, 2930, 2860, 1746 (C=O), 1467, 1280, 1137, 1062. $^1H$ NMR (600 MHz, $CDCl_3$) δ 4.14 (t, J=7.2 Hz, 2H), 3.48 (ddd, J=9.0, 7.2, 6.6 Hz, 2H), 3.35 (ddd, J=9.0, 7.2, 6.6 Hz, 2H), 1.65-1.63 (m, 2H), 1.59-1.54 (m, 4H), 1.49 (s, 3H), 1.35-1.24 (m, 18H), 0.86 (t, J=7.2 Hz, 9H); $^{13}C$ NMR (150 MHz, $CDCl_3$) δ 170.2, 99.5, 65.4, 62.6, 31.7, 31.3, 29.7, 28.5, 25.8, 25.5, 22.6, 22.5, 21.9, 14.0, 13.9.

b. Synthesis of 2,2-bis(hexyloxy)propan-1-ol

To a mixture of $LiAlH_4$ (3.44 g, 90.5 mmol) in $Et_2O$ (200 mL) is added a solution of ester 3 (29.5 g, 82.3 mmol) in $Et_2O$ (100 mL). After addition, the mixture is refluxed for 6 hours. The reaction mixture is cooled to 0° C. and quenched with ethyl acetate (20 mL) and $H_2O$ (20 mL). The mixture is added to saturated potassium sodium tartrate (300 mL) and stirred at 23° C. for 12 hours. The mixture is extracted with $Et_2O$ (2×200 mL) and the combined organic layers are dried over anhydrous sodium sulfate. The solvent is removed and the residue is purified by silica gel chromatography (1→10% ethyl acetate/hexane) to give 2,2-bis(hexyloxy)propan-1-ol 4 (20.6 g, 94%) as a colorless oil: $R_f$(15% EtOAc/hexane)=0.20; IR (thin film, $cm^{-1}$) 3430, 2955, 2929, 2859, 1467, 1378, 1244, 1155, 1112, 1064, 876; $^1H$ NMR (600 MHz, $C_6D_6$) δ 3.58 (d, J=6.6 Hz, 2H), 3.43 (t, J=6.6 Hz, 4H), 1.58 (t, J=6.6 Hz, 1H), 1.53 (m, 4H), 1.36 (s, 3H), 1.34-1.22 (m, 12H), 0.88 (t, J=7.2 Hz, 6H); $^{13}C$ NMR (150 MHz, $C_6D_6$) δ 101.0, 66.2, 61.3, 32.5, 30.9, 26.8, 23.4, 21.3, 14.6.

c. Synthesis of 2,2-bis(hexyloxy)propyl ethyl sulfite

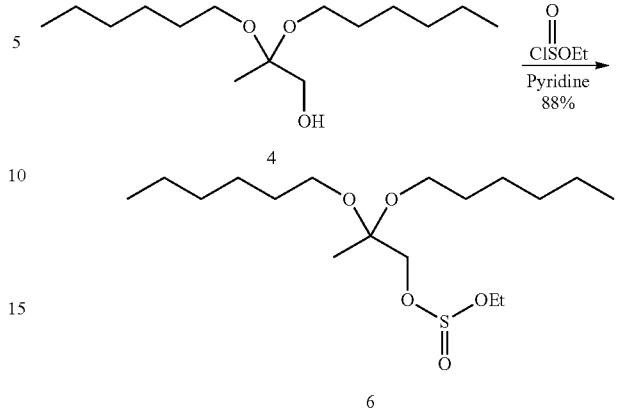

To a solution of alcohol 4 (20.6 g, 79.1 mmol) in $CH_2Cl_2$ (200 mL) is added pyridine (8.12 g, 102.8 mmol) and ethyl chlorosulfite (12.2 g, 94.9 mmol). The reaction mixture is stirred at 23° C. for 10 hours. The reaction is quenched with water (100 mL) and extracted with $CH_2Cl_2$ (2×100 mL). The combined organic layers are washed with HCl (1N, 100 mL), saturated $NaHCO_3$ (100 mL), brine (100 mL) and dried over anhydrous sodium sulfate. The solvent is removed and the residue is purified by silica gel chromatography (1→10% ethyl acetate/hexane) to give 2,2-bis(hexyloxy)propanyl ethyl sulfite 6 (24.5 g, 88%) as a colorless oil: $R_f$(15% EtOAc/hexane)=0.44; IR (thin film, $cm^{-1}$) 2932, 2872, 1467, 1379, 1213, 1194, 1176, 1001, 888; $^1H$ NMR (600 MHz, $CDCl_3$) δ 4.11-4.00 (m, 2H), 3.93 (d, J=10.8 Hz, 1H), 3.77 (d, J=10.8 Hz, 1H), 3.42-3.37 (m, 4H), 1.51-1.48 (m, 4H), 1.33 (s, 3H), 1.31-1.24 (m, 15H), 0.85 (t, J=7.2 Hz, 6H); $^{13}C$ NMR (150 MHz, $CDCl_3$) δ 99.0, 62.9, 60.8, 58.5, 58.3, 31.6, 29.8, 25.9, 22.6, 20.9, 15.3, 14.0.

d. Synthesis of 2,2-bis(hexyloxy)propyl ethyl sulfate

To a solution of sulfite 6 (24.5 g, 69.5 mmol) in MeCN (200 mL), $CH_2Cl_2$ (200 mL) and water (300 mL) is added $NaIO_4$ (29.7 g, 139.0 mmol) and $RuCl_3$ (10 mg, 0.05 mmol). The mixture is stirred at 23° C. for 5 hours. The mixture is filtered through Celite and extracted with $CH_2Cl_2$ (2×200 mL). The combined organic layers are washed with saturated $NaHCO_3$ (100 mL), brine (100 mL) and dried over anhydrous sodium sulfate. The solvent is removed and the residue is purified by silica gel chromatography (1→10% ethyl acetate/hexane) to give 2,2-bis(hexyloxy)propanyl ethyl sulfate 7 (23.3 g, 91%) as a colorless oil: $R_f$ (15% EtOAc/hexane)=0.41; IR (thin film, cm$^{-1}$) 2931, 2860, 1737, 1467, 1403, 1380, 1196, 1179, 1012, 925, 858; $^1$H NMR (600 MHz, CDCl$_3$) δ 4.34 (q, J=7.2 Hz, 2H), 4.09 (s, 2H), 3.43 (ddd, J=9.0, 7.2, 6.6 Hz, 2H), 3.38 (ddd, J=9.0, 7.2, 6.6 Hz, 2H), 1.51 (m, 4H), 1.40 (t, J=7.2 Hz, 3H), 1.37 (s, 3H), 1.34-1.24 (m, 12H), 0.86 (t, J=7.2 Hz, 6H); $^{13}$C NMR (150 MHz, CDCl$_3$) δ 98.2, 72.4, 69.7, 60.9, 31.6, 29.8, 25.9, 22.6, 20.8, 14.5, 14.0.

e. Synthesis of Sodium 2,2-bis(hexyloxy)propyl sulfate

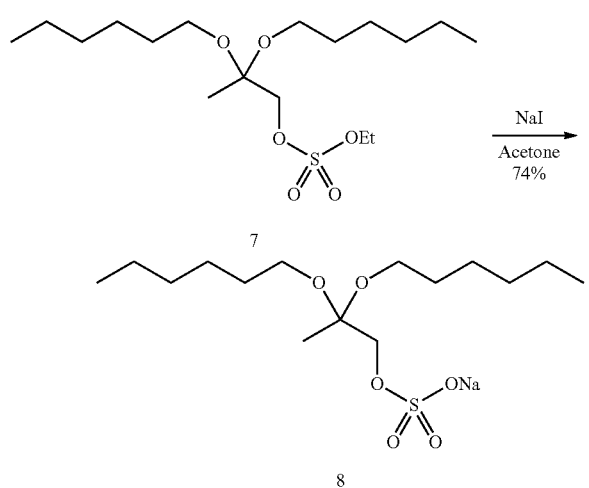

To a solution of sulfate diester 7 (5.6 g, 15.2 mmol) in acetone (15 mL) is added NaI (4.56 g, 30.4 mmol). The solution is stirred at 23° C. for 10 hours. The solvent is removed and the residue is purified by silica gel chromatography (10→100% ethyl acetate/hexane) to give sodium 2,2-bis(hexyloxy)propanyl ethyl sulfate 8 (4.07 g, 74%) as a colorless solid: $R_f$ (20% EtOH/EtOAc)=0.48; IR (thin film, cm$^{-1}$) 3506, 2956, 2930, 2056, 1642, 1467, 1380, 1228, 1015, 820; $^1$H NMR (600 MHz, CDCl$_3$) δ 3.99 (s, 2H), 3.42 (t, J=7.2 Hz, 4H), 1.51-1.49 (m, 4H), 1.36 (s, 3H), 1.30-1.24 (m, 12H), 0.86 (t, J=7.2 Hz, 6H); $^{13}$C NMR (150 MHz, CDCl$_3$) δ 99.2, 69.8, 60.8, 31.8, 29.8, 25.9, 22.7, 20.8, 14.0.

E. Uses for Certain Compounds

In certain embodiments, the anionic acid-labile surfactants may be used to facilitate the solubilization of proteins and other molecules in an aqueous environment. In at least one embodiment, the anionic acid-labile surfactants may be used in purification and identification technologies including, but are not limited to, ion-pair liquid chromatography, liquid chromatography, mass spectrometry (ESI and MALDI MS), liquid-liquid extraction, solid phase extraction, HPLC/MS, HPLC/UV analyses and other techniques that benefit from the removal of the anionic surfactant after use. In at least one embodiment, the anionic acid-labile surfactants may be used in electrophoresis, capillary electrophoresis, electroelution, cell lysis and protein extraction from cell lines, tissues, and biological samples, selective protein extraction from biological samples, extraction of biomolecules from environmental samples, enzymatic digestion of proteins, disruption of protein-protein interactions, and protein denaturation.

In certain embodiments, a method of isolating a sample may generally comprise adjusting the sample to pH 6-12; mixing a solvent and an anionic acid-labile surfactant according to Formula III or Formula IV; contacting the sample with the mixture to form a sample-surfactant complex; cleaving the surfactant from the sample-surfactant complex to form cleavage by-products; and isolating the sample from the cleavage by-products. In at least one embodiment, the method of isolating a sample may comprise agitating at least one of the sample, mixture, and sample-surfactant complex. In at least one embodiment, agitating may comprise sonication. In at least one embodiment, the method of isolating a sample may comprise sonicating the sample-surfactant complex. In at least one embodiment, the method of isolating a sample may comprise performing mass spectrometry on the isolated sample. In at least one embodiment, the cleavage by-products may be soluble in at least one of the cleaved sample-surfactant complex. In at least one embodiment, the cleavage by-products may be soluble in the isolated sample.

In at least one embodiment, the solvent may be selected from the group consisting of water; 0-50% methanol; 0-50% acetonitrile; 5-50 mM ammonium bicarbonate buffer; 5-50 mM Tris-HCl buffer; 5-50 mM sodium phosphate buffer, 5-50 mM ammonium acetate buffer, and any combination thereof.

In at least one embodiment, adjusting the sample to pH 6-12 may comprise contacting the sample with an acid or a base. In at least one embodiment, adjusting the sample to pH 6-12 may comprise contacting the sample with an acid with the proviso that the acid is not a strong acid. In at least one embodiment, adjusting the sample to pH 6-12 may comprise contacting the sample with a weak acid. In at least one embodiment, the acid may be selected from the group consisting of formic acid, acetic acid, trifluoroacetic acid, heptafluorobutyric acid, citric acid, phosphoric acid, and boric acid. In at least one embodiment, the base may be selected from the group consisting of ammonium hydroxide, sodium hydroxide, and potassium hydroxide.

In at least one embodiment, cleaving may comprise adjusting the sample-surfactant complex to pH 2-3. In at least one embodiment, adjusting to pH 2-3 may comprise contacting the sample-surfactant complex with an acid. In at least one embodiment, the adjusting to pH 2-3 may comprise contacting the sample-surfactant complex with an acid with the proviso that the acid in not a strong acid. In at least one embodiment, adjusting to pH 2-3 may comprise contacting the sample-surfactant complex with a weak acid. In at least one embodiment, the acid may be selected from the group consisting of formic acid, trifluoroacetic acid, heptafluorobutyric acid, and acetic acid.

In at least one embodiment, cleaving may comprise incubating the sample-surfactant complex. In at least one embodiment, cleaving may comprise incubating the sample-surfactant complex for less than four (4) hours at less than 99° C. In at least one embodiment, cleaving may comprise incubating the sample-surfactant complex from 5 minutes to 1 (one) hour. In at least one embodiment, cleaving may comprise incubating the sample-surfactant complex from 4-50° C. In at least one embodiment, cleaving may comprise incubating the sample-surfactant complex from 4° C. to room temperature. In at least one embodiment, cleaving may comprise incubating the sample-surfactant complex for 10-30 minutes at 4-50° C. In at least one embodiment, cleaving may comprise incubating for 10 minutes at room temperature.

In certain embodiments, isolating the sample from the cleavage by-products may comprise performing purification and/or identification technologies. In at least one embodiment, isolating the sample from the cleavage by-products may comprise at least one of reversed phase sample clean-up techniques and solid phase extraction techniques. In at least one embodiment, isolating the sample from the cleavage by-products may be selected from the group consisting of ion exchange, hydrophilic interaction, reversed phase chromatographic preparations, and any combination thereof.

In certain embodiments the method of isolating a sample may comprise performing electrokinetic transport of the sample-surfactant complex. In at least one embodiment, performing electrokinetic transport may comprise electrophoresis. In at least one embodiment, electrophoresis may comprise gel electrophoresis, free zone electrophoresis, and capillary electrophoresis. In at least one embodiment, electrophoresis may comprise polyacrylamide gel electrophoresis, including the tube, slab gel and capillary formats of polyacrylamide gel electrophoresis.

In certain embodiments the method of isolating a sample may comprise purifying the isolated sample. In at least one embodiment, purifying may comprise conventional separation methods, including, but not limited to, liquid-liquid extraction, solid-phase extraction and liquid chromatography.

In certain embodiments the method of isolating a sample may comprise performing enzymatic digestion of the sample-surfactant complex. In at least one embodiment, performing enzymatic digestion may comprise forming a sample-surfactant complex by contacting a sample and an acid-labile surfactant according to Formula III or Formula IV (final concentration of 0.01-1.0%) in a buffered solution of 10-100 mM ammonium bicarbonate; incubating the sample-surfactant complex with dithiothreitol (DTT) (5-50 mM) for less than one (1) hour at 50-60° C. for reduction of cysteine-cysteine disulfide linkages; cooling the sample-surfactant complex mixture; incubating the sample-surfactant complex mixture with iodoacetamide (25-250 mM) for less than one (1) hour at less than 30° C. in limited light; mixing the sample-surfactant complex with an enzyme; and incubating the mixture for less than 24 hours at 20-40° C. with shaking. In at least one embodiment, performing enzymatic digestion may comprise incubating the sample-surfactant complex in 50 mM ammonium bicarbonate for 30 minutes at 55° C. with 5 mM DTT; cooling the sample-surfactant complex to room temperature; incubating the sample-surfactant complex for 30 minutes at room temperature in the dark in 25 mM iodoacetamide; mixing the sample-surfactant complex with an enzyme; and incubating the mixture for 4-12 hours at 37° C. with shaking. In at least one embodiment, the enzyme may be selected from the group consisting of trypsin, Glu-C, Arg-C, Lys-C, Asp-N, chymotrypsin, and pepsin.

In at least one embodiment, performing enzymatic digestion may comprise incubating the sample-surfactant complex for less than one (1) hour at less than 99° C.; cooling the sample-surfactant complex; incubating the sample-surfactant complex for less than one (1) hour at less than 99° C. in limited light; mixing the sample-surfactant complex with an enzyme; and incubating the mixture for less than 12 hours at 4-55° C. with shaking. In at least one embodiment, performing enzymatic digestion may comprise incubating the sample-surfactant complex for 30 minutes at 55° C.; cooling the sample-surfactant complex to room temperature; incubating the sample-surfactant complex for 30 minutes at room temperature in the dark; mixing the sample-surfactant complex with an enzyme; and incubating the mixture for 4-8 hours at 37° C. with shaking.

In certain embodiments the method of isolating a sample may further comprise desalting the sample-surfactant complex with an enzyme. In at least one embodiment, desalting may comprise cleaving the sample-surfactant complex. In at least one embodiment, desalting may comprise degrading the surfactant of the sample-surfactant complex. In at least one embodiment, desalting may comprise loading the mixture of the sample and degraded surfactant onto a solid phase extraction chromatographic media; washing away the salts and surfactant degradation products, and collecting the sample from the solid phase extraction media by elution. In at least one embodiment, the solid phase extraction media may be selected from the group consisting of reversed phase, ion exchange, hydrophilic interaction (HILIC), and any combination thereof.

In certain embodiments, a method for analyzing a sample may generally comprise contacting a sample with an anionic acid-labile surfactant according to Formula III or Formula IV to form a sample-surfactant complex and analyzing the sample-surfactant complex. In at least one embodiment, analyzing may comprise purification and/or identification technologies. In at least one embodiment, analyzing may comprise at least one of electrophoresis, electroelution, high performance liquid chromatography, mass spectrometric detection, liquid-liquid extraction, solid phase extraction, and ion-pair liquid chromatography. In at least one embodiment, the method for analyzing a sample may generally comprise degrading the surfactant. In at least one embodiment, the method for analyzing a sample may generally comprise purifying the sample after degrading the surfactant.

In certain embodiments, a method for performing electrophoresis may generally comprise contacting a sample with an anionic acid-labile surfactant according to Formula III or Formula IV to form a sample-surfactant complex, performing electrophoresis on the sample-surfactant complex, and degrading the surfactant after electrophoresis. In at least one embodiment, degrading may comprise contacting the surfactant with an acidic solution. In at least one embodiment, degrading may comprise contacting the surfactant with an acid with the proviso that the acid is not a strong acid. In at least one embodiment, the method for performing electrophoresis may generally comprise purifying the sample after degrading the surfactant.

E. EXAMPLES

The various embodiments of anionic acid-labile surfactants and methods of use described herein may be better understood when read in conjunction with the following representative examples. The following examples are included for purposes of illustration and not limitation.

Comparisons of certain embodiments of anionic acid-labile surfactants and commercially available cleavable surfactants are described. Cleavable surfactants generally exhibit various properties, including, but not limited to, lability (rate, efficiency, cleavage products), compatibility with mass spectrometry (level of signal suppression, adduct formation, artifact peaks, sample prep requirements) and other purification and identification technologies, such as polyacrylamide gel electrophoresis and mass spectrometry detection, and detergent strength and utility (CMC, ability to perform electrophoresis).

The commercially available cleavable surfactants include PPS, available from Protein Discovery, Knoxville, Tenn., Proteamax, available from Promega, Madison, Wis., and Rapigest, available form Waters, Milford, Mass. Proteasmax and Rapigest are anionic acid labile surfactants and PPS is a zwitterionic acid labile surfactant.

1. Protein Scores from in-solution Digestion of BSA

Protein scores from in-solution digestion of BSA in buffers containing an embodiment of an anionic acid-labile surfactant ("AALS-6") and three commercially available acid labile surfactants are illustrated in FIG. 2. A tryptic digestion of 250 pmol BSA is performed using 0.05% AALS-6 in digestion buffer. For the other surfactants, digestion is performed according to the manufacturer's protocols. Sample clean-up and MALDI spotting is performed using C18 reversed phase tips. MALDI-TOF spectra are acquired using an ABI 4800 mass spectrometer in the reflector mode. Protein identification is accomplished through peptide mass fingerprinting (PMF) of the acquired MS spectra.

As shown in FIG. 2, AALS-6 has an average protein score of 93. Algorithms that compare mass spectrometric data to database for protein identification compare the experimental tandem mass spectra against theoretical mass spectra from all peptides and proteins present in the databases. As an output for the database correlation analysis, a protein identification score is generated for each potential protein match. Protein matches are required to have a minimum protein score to be considered a potential positive and significant protein identification. The higher the score, the more likely that the protein identification is real and not a result of random events that match the database. Comparison of the protein scores for two samples that are identified as the same protein gives an indication of the quality of the data that led to the positive protein identification. Samples that contain contaminants or a lower amount of sample protein produce lower quality mass spectra, which in turn may lead to lower protein ID scores. AALS-6 has a higher average protein score than the other 3 commercially available surfactants, indicating that the quality of the digested protein sample presented to the mass spectrometer is of higher quality for the AALS-6 sample. The higher protein ID scores suggest that the digestion of the BSA protein is more complete, producing a larger number of peptides for delivery to the mass spectrometer, which produces more complete mass spectrometric data.

2. Protein Scores from in-solution Digestion of Ovalbumin

The protein scores from in-solution digestion of ovalbumin in buffers containing an embodiment of an anionic acid-labile surfactant ("AALS-6") and three commercially available acid labile surfactants are illustrated in FIG. 3. A tryptic digestion of 250 µmol ovalbumin was performed using 0.05% AALS-6 in digestion buffer. For the other surfactants, digestion was performed according to the manufacturer's protocols. Sample clean-up and MALDI spotting was performed using C18 reversed phase tips. MALDI-TOF MS and MS/MS spectra were acquired using an ABI 4800 mass spectrometer in the reflector mode. Protein identification was accomplished through database searching MS/MS spectra using Mascot search engine.

As shown in FIG. 3, AALS-6 has an average protein score of 487 and the conventional acid labile surfactants have average protein scores of 329 (ProteasMax), 341 (Rapigest), and 166 (PPS). The ovalbumin control digestion score is 347. In general, the higher protein score indicates an increase in the quality and/or completeness of the digestion because more peptides are available for analysis by the mass spectrometer, and/or the quality of the digested sample delivered to the mass spectrometer is increased. Without intending to be bound by any particular theory, the higher protein score of AALS-6 may be due is due to its detergent characteristics, e.g., critical micellular concentration of 7.7 mM, which may improve both the solubility of the sample and the extent of denaturation of its 3-dimensional structure by providing improved enzyme access to the cleavage points. The higher protein score of AALS-6 may also be due to its degradation kinetics. For example, once the digestion experiment is complete, the degradation of the surfactant reduces contamination of the signal by detergent molecules and by-products as well as reduces the ion suppression effects commonly seen in mass spectrometry analysis of peptides and proteins.

3. Protein Electroelution

An embodiment of an anionic acid-labile surfactant ("AALS-6") is used for protein electroelution from a polyacrylamide gel using Protea's GPR-800 system. A gel spot comprising the protein is placed in the gel loading reservoirs. A 0.5% anionic acid-labile surfactant is prepared by mixing the anionic acid-labile surfactant with Tris-glycine buffer. The mixture is placed in the gel loading reservoir to form a protein-surfactant complex (sample-surfactant complex). The protein-surfactant complex exhibits a blue color from the Coomassie blue dye molecules that are associated with the protein during the staining process. The mixture is used to transfer a protein from a coomassie stained gel into solution when voltage is applied to the sample. The movement of the protein-surfactant complex is tracked by the disappearance of the blue color of coomassie from the gel loading reservoirs and the emergence of the blue color of coomassie in the sample collection reservoirs. The movement of the protein-surfactant is complete after 15 min. The presence of the protein in the collection reservoirs is confirmed by MALDI-TOF mass spectrometry.

Similar experiments are performed with three (3) conventional anionic acid-labile surfactants. A 0.5% Proteamax, 0.5% Rapigest, and 0.5% PPS are prepared by mixing the surfactants with Tris-glycine buffer. No protein is detected by MALDI-TOF mass spectrometry in the collection reservoirs after 15 min for the 0.5% Proteamax and 0.5% Rapigest. No movement of the protein-coomassie complex is detectable for the 0.5% PPS surfactant.

4. Degradation Time V. Signal-to-noise Ratio

Referring to FIG. 1, the degradation time versus signal-to-noise ratio is compared for a certain embodiment of an anionic acid-labile surfactant ("AALS-6") and three commercially available acid-labile surfactants. A 0.1% of each surfactant is mixed with 20 pmol Myoglobin and degraded for 0, 5, 10, 15, 30, 45, 60, 90, 120 and 240 min. The samples are spotted onto a MALDI target using C8 reversed phase tips. MALDI-TOF spectra are acquired using an ABI 4800 mass spectrometer in the linear mode.

As shown in FIG. 1, the anionic acid-labile surfactant may improve the sensitivity of mass spectrometry analysis of proteins in the presence of the degraded anionic acid-labile surfactants. Cleavage of these anionic acid-labile surfactants may eliminate the detergent properties that induce signal suppression and/or create signal adducts in the mass spectra. Adduct peaks in mass spectra may result from a population of surfactant-protein complexes containing different numbers of surfactant molecules per protein, resulting in many different complexes (with different masses) to be detected. If there is no surfactant present to form a surfactant-protein complex, then these adducts may not be formed or observed. This mechanism demonstrates the utility for removing surfactants by cleavage to improve mass spectrometry analysis. These effects may increase the signal intensity of analytes and eliminate the suppressive effects of conventional detergents.

All documents cited herein are, in relevant part, incorporated herein by reference, but only to the extent that the incorporated material does not conflict with existing definitions, statements, or other documents set forth herein. To the extent that any meaning or definition of a term in this document conflicts with any meaning or definition of the same term in a document incorporated by reference, the meaning or definition assigned to that term in this document shall govern. The citation of any document is not to be construed as an admission that it is prior art with respect to the anionic acid-labile surfactants and methods of use described herein.

While particular exemplary embodiments of anionic acid-labile surfactants and methods of use have been illustrated and described, it would be obvious to those skilled in the art that various other changes and modifications can be made without departing from the spirit and scope of the invention. Those skilled in the art will recognize, or be able to ascertain using no more than routine experimentation, numerous equivalents to the specific devices and methods described herein, including alternatives, variants, additions, deletions, modifications and substitutions. This disclosure, including the claims, is intended to cover all such equivalents that are within the spirit and scope of this invention.

What is claimed is:

1. A method of cleaving a compound of the formula:

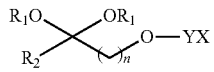

wherein $R_1$ is independently selected from —$(CH_2)_{0-9}CH_3$, $R_2$ is selected from the group consisting of —H and —$(CH_2)_{0-5}CH_3$, Y is selected from the group consisting of —$SO_3^-$ and —$PO_3^-$, X is a cation selected from the group consisting of sodium, potassium, lithium, and ammonium ions, and n is an integer from 1 to 8, the method comprising contacting the compound and an acid.

2. The method of claim 1, wherein each $R_1$ is —$(CH_2)_5 CH_3$, $R_2$ is —$CH_3$, and n is 1.

3. The method of claim 1, wherein each $R_1$ is —$(CH_2)_6 CH_3$, $R_2$ is —$CH_3$, and n is 1.

4. The method of claim 1, wherein each $R_1$ is —$(CH_2)_5 CH_3$, $R_2$ is —$CH_3$, Y is —$SO_3^-$, X is sodium, and n is 1.

5. The method of claim 1, wherein each $R_1$ is —$(CH_2)_6 CH_3$, $R_2$ is —$CH_3$, Y is —$SO_3^-$, X is sodium, and n is 1.

6. A method of solubilizing a sample selected from the group consisting of hydrophobic molecules, proteins, peptides, polypeptides, polymers, nucleic acids, lipids, lipophilic cellular components, hydrophilic extracellular components, and any combinations thereof, the method comprising contacting the sample and a compound of the formula:

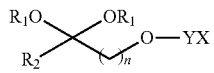

wherein $R_1$ is independently selected from —$(CH_2)_{0-9}CH_3$, $R_2$ is selected from the group consisting of —H and —$(CH_2)_{0-5}CH_3$, Y is selected from the group consisting of —$SO_3^-$ and —$PO_3^-$, X is a cation selected from the group consisting of sodium, potassium, lithium, and ammonium ions, and n is an integer from 1 to 8.

7. The method of claim 6, wherein each $R_1$ is —$(CH_2)_5 CH_3$, $R_2$ is —$CH_3$, and n is 1.

8. The method of claim 6, wherein each $R_1$ is —$(CH_2)_6 CH_3$, $R_2$ is —$CH_3$, and n is 1.

9. The method of claim 6, wherein each $R_1$ is —$(CH_2)_5 CH_3$, $R_2$ is —$CH_3$, Y is —$SO_3^-$, X is sodium, and n is 1.

10. The method of claim 6, wherein each $R_1$ is —$(CH_2)_6 CH_3$, $R_2$ is —$CH_3$, Y is —$SO_3^-$, X is sodium, and n is 1.

11. A method of isolating a sample selected from the group consisting of hydrophobic molecules, proteins, peptides, polypeptides, polymers, nucleic acids, lipids, lipophilic cellular components, hydrophilic extracellular components, and any combinations thereof, the method comprising:
adjusting the sample to pH 6-12;
mixing a solvent with a compound of the formula:

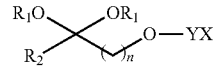

wherein $R_1$ is independently selected from —$(CH_2)_{0-9}CH_3$, $R_2$ is selected from the group consisting of —H and —$(CH_2)_{0-5}CH_3$, Y is selected from the group consisting of —$SO_3^-$ and —$PO_3^-$, X is a cation is selected from the group consisting of sodium, potassium, lithium, and ammonium ions, and n is an integer from 1 to 8;
contacting the sample with the mixture to form a sample-surfactant complex;
cleaving the surfactant from the sample-surfactant complex to form cleavage by-products; and
isolating the sample from the cleavage by-products.

12. The method of claim 11, wherein the cleaving comprises:
adjusting the sample-surfactant complex to pH 2-3; and
incubating the sample-surfactant complex for 10-30 minutes at 4-50° C.

13. The method of claim 11, wherein the solvent is selected from the group consisting of water; 0-50% methanol; 0-50% acetonitrile; 5-50 mM ammonium bicarbonate buffer; 5-50 mM Tris-HCl buffer; 5-50 mM sodium phosphate buffer; 5-50 mM ammonium acetate buffer; and any combination thereof.

14. The method of claim 11, wherein the isolating comprises at least one of reversed phase sample clean-up techniques and solid phase extraction techniques.

15. The method of claim 11 comprising performing electrokinetic transport of the sample-surfactant complex.

16. The method of claim 15, wherein the performing electrokinetic transport is electrophoresis.

17. The method of claim 11 comprising performing enzymatic digestion of the sample-surfactant complex.

18. The method of claim 17, wherein the performing enzymatic digestion comprises:
incubating the sample-surfactant complex for less than one hour at 50-60° C.;
cooling the sample-surfactant complex to room temperature;
incubating the sample-surfactant complex for less than one hour at less than 30° C. in limited light;
mixing the sample-surfactant complex with an enzyme; and
incubating the mixture for less than 24 hours at 20-40° C. with shaking.

19. The method of claim 18 comprising desalting the sample-surfactant complex with an enzyme.

20. The method of claim 18 comprising performing mass spectrometry on the isolated sample.

* * * * *